US012648761B2

(12) United States Patent
Duan et al.

(10) Patent No.: US 12,648,761 B2
(45) Date of Patent: Jun. 9, 2026

(54) SYSTEMS AND METHODS FOR IMAGE COMPENSATION IN ULTRASOUND IMAGING

(71) Applicant: WUHAN UNITED IMAGING HEALTHCARE CO., LTD., Wuhan (CN)

(72) Inventors: Xueli Duan, Wuhan (CN); Yuyu Zhou, Shanghai (CN); Zuowei Yang, Wuhan (CN)

(73) Assignee: WUHAN UNITED IMAGING HEALTHCARE CO., LTD., Wuhan (CN)

( * ) Notice: Subject to any disclaimer, the term of this patent is extended or adjusted under 35 U.S.C. 154(b) by 76 days.

(21) Appl. No.: 18/399,640

(22) Filed: Dec. 28, 2023

(65) Prior Publication Data

US 2024/0215955 A1      Jul. 4, 2024

(30) Foreign Application Priority Data

Dec. 29, 2022    (CN) .......................... 202211703558.7

(51) Int. Cl.
*A61B 8/00* (2006.01)

(52) U.S. Cl.
CPC ................................. *A61B 8/5207* (2013.01)

(58) Field of Classification Search
None
See application file for complete search history.

(56) References Cited

U.S. PATENT DOCUMENTS

| | | | |
|---|---|---|---|
| 8,090,165 B2 * | 1/2012 | Jiang | G06T 5/40 |
| | | | 382/128 |
| 2003/0187353 A1 | 10/2003 | Ng et al. | |
| 2006/0058657 A1 | 3/2006 | Sathyanarayana | |
| 2007/0088213 A1 * | 4/2007 | Poland | G10K 11/34 |
| | | | 600/437 |
| 2008/0123986 A1 | 5/2008 | Jiang et al. | |
| 2010/0240992 A1 * | 9/2010 | Hao | G01S 7/5205 |
| | | | 600/437 |

(Continued)

FOREIGN PATENT DOCUMENTS

| | | |
|---|---|---|
| CN | 113014827 A | 6/2021 |
| JP | 2005152422 A | 6/2005 |

OTHER PUBLICATIONS

First Office Action in Chinese Application No. 202211703558.7 mailed on Sep. 24, 2025, 15 pages.

*Primary Examiner* — Nyrobi Celestine
(74) *Attorney, Agent, or Firm* — METIS IP LLC

(57) ABSTRACT

Systems and methods for ultrasound imaging are provided. The methods may include generating ultrasound images of a target subject by performing an ultrasound imaging on the target subject. The ultrasound imaging may at least include a first period and a second period following the first period, and the second period is set by a parameter update instruction. An ultrasound image acquired in the first period may be generated using first compensation parameters. An ultrasound image acquired in the second period may be generated using second compensation parameters, and the second compensation parameters are determined based on compensation parameters of the previous ultrasound image.

20 Claims, 8 Drawing Sheets

500

(56)      References Cited

U.S. PATENT DOCUMENTS

| | | | |
|---|---|---|---|
| 2011/0144501 A1* | 6/2011 | Nishimura | A61B 8/13 600/443 |
| 2013/0030298 A1* | 1/2013 | Tamura | A61B 8/4254 600/442 |
| 2015/0103108 A1 | 4/2015 | Seong et al. | |
| 2016/0157827 A1* | 6/2016 | Kristoffersen | A61B 8/5207 600/443 |
| 2016/0206291 A1* | 7/2016 | Yang | A61B 8/5253 |
| 2016/0345936 A1* | 12/2016 | Cho | G01S 7/52063 |
| 2018/0220995 A1* | 8/2018 | Pelissier | A61B 8/5207 |
| 2018/0313954 A1* | 11/2018 | Gyöngy | G01S 7/52046 |
| 2021/0093301 A1* | 4/2021 | Wang | A61B 8/463 |
| 2023/0015623 A1* | 1/2023 | Loupas | G01S 15/8979 |

* cited by examiner

400

500

<u>700</u>

SYSTEMS AND METHODS FOR IMAGE COMPENSATION IN ULTRASOUND IMAGING

CROSS-REFERENCE TO RELATED APPLICATIONS

This application claims priority to Chinese Patent Application No. 202211703558.7 filed on Dec. 29, 2022, the entire contents of which are hereby incorporated by reference.

TECHNICAL FIELD

The present disclosure generally relates to ultrasonic imaging, and more particularly, relates to systems and methods for image compensation in ultrasound imaging.

BACKGROUND

An ultrasonic image of internal tissues of a target subject may be obtained by performing ultrasound imaging on the target subject using ultrasonic waves. Due to energy attenuation of the ultrasonic waves, ultrasound echo signals from tissues at different depths detected by the ultrasound probe have different amplitudes. For example, the amplitude of ultrasound echo signals from deep tissues is smaller than the amplitude of ultrasound echo signals from shallow tissues, which makes that in the ultrasound image, a region corresponding to the shallow tissues is relatively brighter while a region corresponding to the deep tissues is relatively darker. Therefore, it is necessary to perform a time gain compensation (TGC) (e.g., an analog time gain compensation (ATGC), a digital time gain compensation (DTGC)) on the ultrasound echo signals from tissues at different depths, so that the tissues at different depths appear relatively consistent in brightness in the ultrasound image.

SUMMARY

An aspect of the present disclosure relates to a method for ultrasonic imaging. The method may be implemented on a computing device including at least one processor and at least one storage device. The method may include generating ultrasound images of a target subject by performing an ultrasound imaging on the target subject. The ultrasound imaging may at least include a first period and a second period following the first period, and the second period is set by a parameter update instruction. An ultrasound image acquired in the first period may be generated using first compensation parameters. An ultrasound image acquired in the second period may be generated using second compensation parameters, and the second compensation parameters are determined based on compensation parameters of the previous ultrasound image obtained immediately before the ultrasound image acquired in the second period.

In some embodiments, for the ultrasound image acquired in the second period, the corresponding second compensation parameters are determined by obtaining the previous ultrasound image and the compensation parameters of the previous ultrasound image; determining current compensation parameters by comparing pixel information of the previous ultrasound image and reference pixel information; and determining the second compensation parameters based on the compensation parameters of the previous ultrasound image and the current compensation parameters.

In some embodiments, the reference pixel information includes pixel information of an ideal image of the target subject acquired based on ideal compensation parameters.

In some embodiments, the pixel information of the previous ultrasound image is determined by dividing the previous ultrasound image into multiple sub-image regions; determining a median pixel value of each of the multiple sub-image regions; and determining the pixel information of the previous ultrasound image based on median pixel values corresponding to the multiple sub-image regions.

In some embodiments, the determining the second compensation parameters based on the compensation parameters of the previous ultrasound image and the current compensation parameters includes determining a degree of difference between the compensation parameters of the previous ultrasound image and the current compensation parameters; and determining the second compensation parameters based on a determination result of whether the degree of difference is smaller than or equal to a preset threshold.

In some embodiments, the degree of difference is a mean square error of the compensation parameters of the previous ultrasound image and the current compensation parameters.

In some embodiments, the determination result includes that the degree of difference is smaller than or equal to the preset threshold, and the determining the second compensation parameters includes designating the compensation parameters of the previous ultrasound image as the second compensation parameters.

In some embodiments, the determination result includes that the degree of difference is larger than the preset threshold, and the determining the second compensation parameters includes determining a weighted sum of the compensation parameters of the previous ultrasound image and the current compensation parameters, and designating the weighted sum as the second compensation parameters.

In some embodiments, weights of the compensation parameters of the previous ultrasound image and the current compensation parameters are determined based on the degree of difference.

In some embodiments, the second period of the ultrasound imaging is performed by in response to determining that the parameter update instruction is received, obtaining the previous ultrasound image and the compensation parameters of the previous ultrasound image; determining current compensation parameters by comparing pixel information of the previous ultrasound image and reference pixel information; determining the second compensation parameters based on the compensation parameters of the previous ultrasound image and the current compensation parameters; generating the ultrasound image acquired in the second period using the second compensation parameters; and designating the ultrasound image acquired in the second period and the second compensation parameters as the previous ultrasound image and the compensation parameters of the previous ultrasound image to perform a next second period until the parameter update instruction is stopped.

In some embodiments, the method further includes in response to determining that the parameter update instruction is stopped, initiating a next first period of the ultrasound imaging to obtain the first compensation parameters and generate a next ultrasound image acquired in the next first period using the first compensation parameters.

In some embodiments, the first compensation parameters and the second compensation parameters are digital time gain compensation (DTGC) parameters.

In some embodiments, the second compensation parameters are represented by a curve or a function indicating a relationship between the digital time gain compensation (DTGC) parameters and imaging depths.

A further aspect of the present disclosure relates to an ultrasound imaging system. The system may include an ultrasound imaging device, at least one storage device including a set of instructions, and at least one processor in communication with the at least one storage device. When executing the set of instructions, the at least one processor may be directed to cause the system to implement operations. The operations may include generating ultrasound images of a target subject by performing an ultrasound imaging on the target subject. The ultrasound imaging may at least include a first period and a second period following the first period, and the second period is set by a parameter update instruction. An ultrasound image acquired in the first period may be generated using first compensation parameters. An ultrasound image acquired in the second period may be generated using second compensation parameters, and the second compensation parameters are determined based on compensation parameters of the previous ultrasound image obtained immediately before the ultrasound image acquired in the second period.

A still further aspect of the present disclosure relates to a method for ultrasonic imaging. The method may be implemented on a computing device including at least one processor and at least one storage device. The method may include in response to determining that a parameter update instruction is received, obtaining a previous ultrasound image and compensation parameters of the previous ultrasound image; determining second compensation parameters based on the compensation parameters of the previous ultrasound image; generating a second ultrasound image using the second compensation parameters; and designating the second ultrasound image and the second compensation parameters as the previous ultrasound image and the compensation parameters of the previous ultrasound image to determine a next second compensation parameters and generate a next second ultrasound image until the parameter update instruction is stopped.

In some embodiments, determining second compensation parameters based on the compensation parameters of the previous ultrasound image includes determining current compensation parameters by comparing pixel information of the previous ultrasound image and reference pixel information; and determining the second compensation parameters based on the compensation parameters of the previous ultrasound image and the current compensation parameters.

In some embodiments, the pixel information of the previous ultrasound image is determined by dividing the previous ultrasound image into multiple sub-image regions; determining a median pixel value of each of the multiple sub-image regions; and determining the pixel information of the previous ultrasound image based on median pixel values corresponding to the multiple sub-image regions.

In some embodiments, the determining the second compensation parameters based on the compensation parameters of the previous ultrasound image and the current compensation parameters includes determining a degree of difference between the compensation parameters of the previous ultrasound image and the current compensation parameters, the degree of difference being a mean square error of the compensation parameters of the previous ultrasound image and the current compensation parameters; and determining the second compensation parameters based on a determination result of whether the degree of difference is smaller than or equal to a preset threshold.

In some embodiments, the method further includes before the parameter update instruction is received, obtaining first compensation parameters; and generating an ultrasound image using the first compensation parameters.

In some embodiments, the method further includes in response to determining that the parameter update instruction is stopped, obtaining the first compensation parameters; and generating a next first ultrasound image using the first compensation parameters until receiving a next parameter update instruction.

Additional features may be set forth in part in the description which follows, and in part may become apparent to those skilled in the art upon examination of the following and the accompanying drawings or may be learned by production or operation of the examples. The features of the present disclosure may be realized and attained by practice or use of various aspects of the methodologies, instrumentalities, and combinations set forth in the detailed examples discussed below.

BRIEF DESCRIPTION OF THE DRAWINGS

The present disclosure is further described in terms of exemplary embodiments. These exemplary embodiments are described in detail with reference to the drawings. The drawings are not to scale. These embodiments are non-limiting exemplary embodiments, in which like reference numerals represent similar structures throughout the several views of the drawings, and wherein.

DETAILED DESCRIPTION

Figure 1:
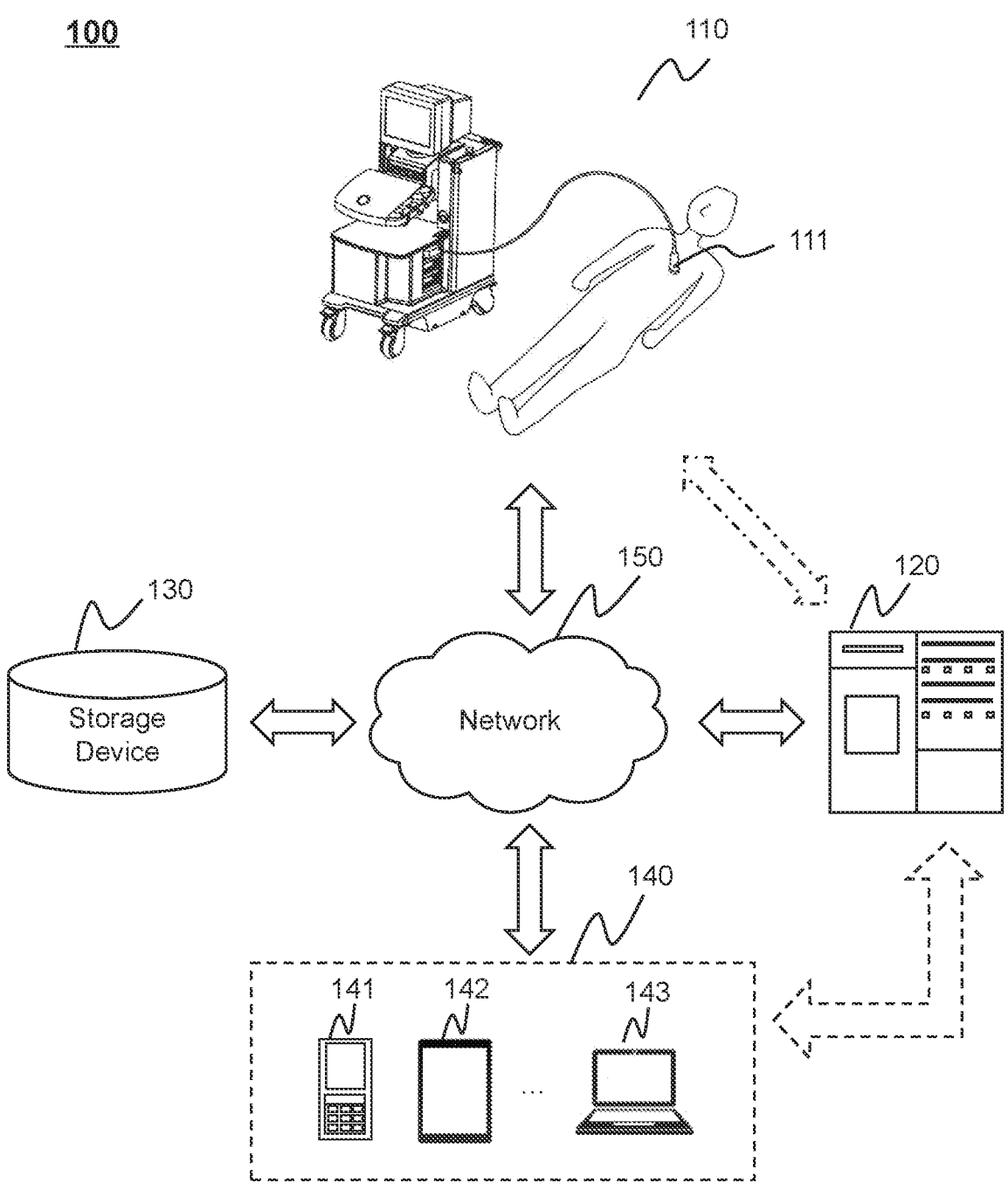
FIG. 1 is a schematic diagram illustrating an exemplary ultrasound imaging system according to some embodiments of the present disclosure.

In the following detailed description, numerous specific details may be set forth by way of examples in order to provide a thorough understanding of the relevant disclosure. However, it should be apparent to those skilled in the art that the present disclosure may be practiced without such details. In other instances, well-known methods, procedures, systems, components, and/or circuitry have been described at a relatively high-level, without detail, in order to avoid unnecessarily obscuring aspects of the present disclosure. Various modifications to the disclosed embodiments may be readily apparent to those skilled in the art, and the general principles defined herein may be applied to other embodiments and applications without departing from the spirit and scope of the present disclosure. Thus, the present disclosure may be not limited to the embodiments shown, but to be accorded the widest scope consistent with the claims.

The terminology used herein may be for the purpose of describing particular example embodiments only and may be not intended to be limiting. As used herein, the singular forms "a," "an," and "the" may be intended to include the plural forms as well, unless the context clearly indicates otherwise. It may be understood that the terms "system," "unit," "module," and/or "block" used herein are one method to distinguish different components, elements, parts, sections or assemblies of different levels in ascending order. However, the terms may be displaced by another expression if they achieve the same purpose.

The modules (or units, blocks, units) described in the present disclosure may be implemented as software and/or hardware modules and may be stored in any type of non-transitory computer-readable medium or other storage devices. In some embodiments, a software module may be compiled and linked into an executable program. It may be appreciated that software modules may be callable from other modules or from themselves, and/or may be invoked in response to detected events or interrupts. Software modules configured for execution on computing devices may be provided on a computer readable medium or as a digital download (and can be originally stored in a compressed or installable format that requires installation, decompression, or decryption prior to execution). Such software code may be stored, partially or fully, on a memory device of the executing computing device, for execution by the computing device. Software instructions may be embedded in a firmware, such as an EPROM. It may be further appreciated that hardware modules (e.g., circuits) may be included in connected or coupled logic units, such as gates and flip-flops, and/or may be included in programmable units, such as programmable gate arrays or processors. The modules or computing device functionality described herein may be preferably implemented as hardware modules, but may be software modules as well. In general, the modules described herein refer to logical modules that may be combined with other modules or divided into units despite their physical organization or storage.

Certain terminology has been used to describe embodiments of the present disclosure. For example, the terms "one embodiment," "an embodiment," and/or "some embodiments" may mean that a particular feature, structure or characteristic described in connection with the embodiment is in at least one embodiment of the present disclosure. Therefore, it is emphasized and should be appreciated that two or more references to "an embodiment" or "one embodiment" or "an alternative embodiment" in various portions of this specification may not necessarily all referring to the same embodiment. Furthermore, the particular features, structures or characteristics may be combined as suitable in one or more embodiments of the present disclosure.

These and other features, and characteristics of the present disclosure, as well as the methods of operation and functions of the related elements of structure and the combination of parts and economies of manufacture, may become more apparent upon consideration of the following description with reference to the accompanying drawings, all of which form a part of this disclosure. It is to be expressly understood, however, that the drawings may be for the purpose of illustration and description only and may be not intended to limit the scope of the present disclosure.

The flowcharts used in the present disclosure may illustrate operations that systems implement according to some embodiments of the present disclosure. It is to be expressly understood, the operations of the flowcharts may be implemented not in order. Conversely, the operations may be implemented in inverted order, or simultaneously. Moreover, one or more other operations may be added to the flowcharts. One or more operations may be removed from the flowcharts.

Generally, during the ultrasound imaging process, time gain compensation (TGC) parameters are manually adjusted by a user (e.g., a doctor) on the basis of default TGC parameters. The user decides whether and how to adjust the default TGC parameters corresponding to one or several tissues at different depths by observing a previous ultrasound image. In practical applications, in order to obtain an ideal ultrasound image, the user is often required to have a rich experience or to perform TGC parameter adjustments repeatedly, which is inefficient and cumbersome.

The present disclosure provides systems and methods that can automatically determine compensation parameters for ultrasound imaging. The systems may generate ultrasound images of a target subject by performing an ultrasound imaging on the target subject. The ultrasound imaging may at least include a first period and a second period following the first period. The second period may be set by a parameter update instruction. An ultrasound image acquired in the first period may be generated using first compensation parameters, and an ultrasound image acquired in the second period may be generated using second compensation parameters. The second compensation parameters may be determined based on compensation parameters of the previous ultrasound image obtained immediately before the ultrasound image acquired in the second period. According to the embodiments of the present disclosure, after being triggered by the parameter update instruction, the compensation parameter adjustment is performed automatically by the ultrasound imaging systems, and the automatic compensation parameter adjustment can be carried out continuously, that is the second compensation parameters of each current ultrasound image can be determined based on the compensation parameters of the previous ultrasound image. The systems and methods disclosed herein can reduce user intervention and improve the accuracy of the second compensation parameters, thereby adaptively obtaining better image optimization results with fewer operations.

FIG. 1 is a schematic diagram illustrating an ultrasound imaging system 100 according to some embodiments of the present disclosure. As shown in FIG. 1, the ultrasound imaging system 100 may include an ultrasound imaging device 110, a processing device 120, a storage device 130, one or more terminals 140, and a network 150. In some embodiments, the ultrasound imaging device 110, the processing device 120, the storage device 130, and/or the terminal(s) 140 may be connected to and/or communicate with each other via a wireless connection, a wired connection, or a combination thereof.

The ultrasound imaging device 110 refers to a medical device that uses ultrasonic waves to reproduce a structure inside the human body as images. Merely by way of example, the ultrasound imaging device 110 may include a Doppler ultrasound diagnosis device, an ultrasound diagnosis instrument, an ultrasound Doppler flow analyzer, etc. In some embodiments, as shown in FIG. 1, the ultrasound imaging device 110 may include an ultrasonic probe 111. The ultrasonic probe 111 may obtain scanning data. Specifically, the ultrasonic probe 111 may emit ultrasonic waves to a target subject or a portion of the target subject and receive reflected ultrasonic waves from the target subject or the portion of the target subject. The reflected ultrasonic waves may be used for generating ultrasound images of the target subject. The ultrasound images may illustrate an internal structure and the health condition of the target subject. It should be noted that the ultrasound imaging device 110 described herein is merely provided for illustration purposes, and not intended to limit the scope of the present disclosure.

In some embodiments, the target subject may include a human being (e.g., a patient), an animal, or a specific portion, organ, and/or tissue thereof. Merely by way of example, the target subject may include head, chest, abdomen, heart, liver, upper limbs, lower limbs, or the like, or any combination thereof. In the present disclosure, the term "object" or "subject" are used interchangeably in the present disclosure.

In some embodiments, the processing device 120 may be a single server or a server group. The server group may be centralized or distributed. The processing device 120 may process data and/or information obtained from the ultrasound imaging device 110, the storage device 130, and/or the terminal(s) 140. For example, the processing device 120 may generate ultrasound images of the target subject by performing an ultrasound imaging on the target subject. As another example, the processing device 120 may determine compensation parameters for generating a current ultrasound image in an ultrasound imaging in response to a parameter update instruction. In some embodiments, the processing device 120 may be local or remote from the ultrasound imaging system 100. In some embodiments, the processing device 120 may be implemented on a cloud platform. In some embodiments, the processing device 120 or a portion of the processing device 120 may be integrated into the ultrasound imaging device 110 and/or the terminal(s) 140. It should be noted that the processing device 120 in the present disclosure may include one or multiple processors. Thus operations and/or method steps that are performed by one processor may also be jointly or separately performed by the multiple processors.

The storage device 130 may store data, instructions, and/or any other information. In some embodiments, the storage device 130 may store data obtained from the ultrasound imaging device 110, the processing device 120, and/or the terminal(s) 140. In some embodiments, the storage device 130 may store data and/or instructions that the processing device 120 may execute or use to perform exemplary methods described in the present disclosure. In some embodiments, the storage device 130 may include a mass storage device, a removable storage device, a volatile read-and-write memory, a read-only memory (ROM), or the like, or a combination thereof. In some embodiments, the storage device 130 may be implemented on a cloud platform. In some embodiments, the storage device 130 may be part of the ultrasound imaging device 110, the processing device 120, and/or the terminal(s) 140.

The terminal(s) 140 may be configured to enable a user interaction between a user and the ultrasound imaging system 100. In some embodiments, the terminal(s) 140 may be connected to and/or communicate with the ultrasound imaging device 110, the processing device 120, and/or the storage device 130. In some embodiments, the terminal(s) 140 may include a mobile device 141, a tablet computer 142, a laptop computer 143, or the like, or a combination thereof. In some embodiments, the terminal(s) 140 may be part of the processing device 120 and/or the ultrasound imaging device 110.

The network 150 may include any suitable network that can facilitate the exchange of information and/or data for the ultrasound imaging system 100. In some embodiments, one or more components of the ultrasound imaging system 100 (e.g., the ultrasound imaging device 110, the processing device 120, the storage device 130, the terminal(s) 140, etc.) may communicate information and/or data with one or more other components of the ultrasound imaging system 100 via the network 150.

It should be noted that the above description is intended to be illustrative, and not to limit the scope of the present disclosure. Many alternatives, modifications, and variations will be apparent to those skilled in the art. The features, structures, methods, and characteristics of the exemplary embodiments described herein may be combined in various ways to obtain additional and/or alternative exemplary embodiments. In some embodiments, the ultrasound imaging system 100 may include one or more additional components and/or one or more components described above may be omitted. Additionally or alternatively, two or more components of the ultrasound imaging system 100 may be integrated into a single component. For example, the processing device 120 may be integrated into the ultrasound imaging device 110. As another example, a component of the ultrasound imaging system 100 may be replaced by another component that can implement the functions of the component. However, those variations and modifications do not depart from the scope of the present disclosure.

Figure 2:
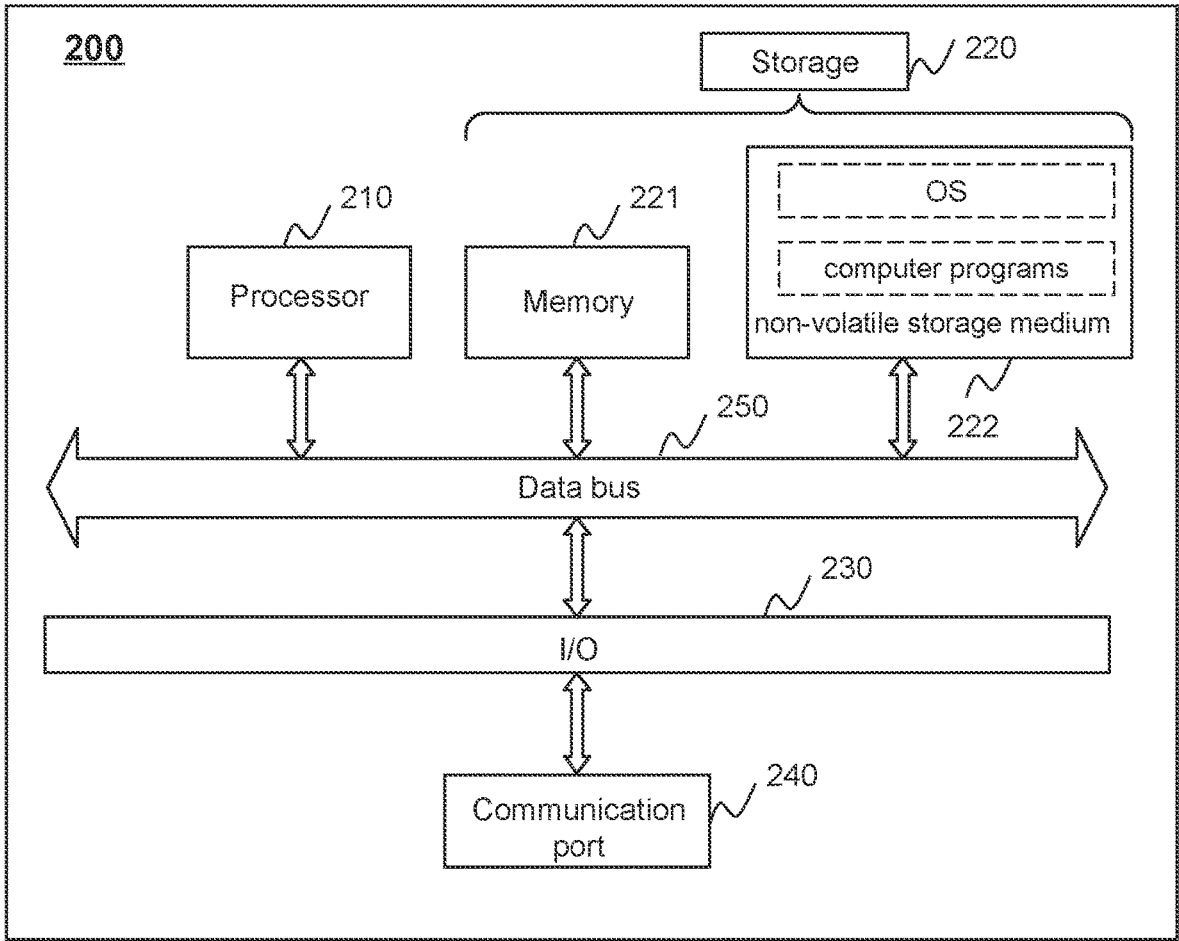
FIG. 2 is a schematic diagram illustrating exemplary hardware and/or software components of a computing device according to some embodiments of the present disclosure.

FIG. 2 is a schematic diagram illustrating exemplary hardware and/or software components of a computing device 200 according to some embodiments of the present disclosure. The computing device 200 may be used to implement any component of the ultrasound imaging system 100 as described herein. For example, the processing device 120 and/or a terminal 140 may be implemented on the computing device 200, respectively, via its hardware, software program, firmware, or a combination thereof. Although only one such computing device is shown, for convenience, the computer functions relating to the ultrasound imaging system 100 as described herein may be implemented in a distributed fashion on a number of similar platforms, to distribute the processing load. As illustrated in FIG. 2, the computing device 200 may include a processor 210, a storage 220, an input/output (I/O) 230, a communication port 240, and a data bus 250.

The processor 210 may execute computer instructions (e.g., program code) and perform functions of the processing device 120 in accordance with techniques described herein. The storage 220 may store data/information obtained from the ultrasound imaging device 110, the storage device 130, the terminal(s) 140, and/or any other component of the ultrasound imaging system 100. In some embodiments, the storage 220 may store one or more programs and/or instructions to perform exemplary methods described in the present disclosure. In some embodiments, the storage 220 may include a memory 221 and a non-volatile storage medium 222. In some embodiments, the non-volatile storage medium 222 may store an operating system (OS) (e.g., iOS™, Android™, Windows Phone™, etc.), computer programs. The I/O 230 may input and/or output signals, data, information, etc. In some embodiments, the I/O 230 may enable a user interaction with the processing device 120. In some embodiments, the I/O 230 may include an input device by which the user may input the signals, data, and/or information. In some embodiments, the I/O 230 may include a display by which the computing device 200 may output the signals, data, and/or information. The communication port 240 may be connected to a network (e.g., the network 150) to facilitate data communications. The data bus 250 may be configured to implement data communications among components of the computing device 200.

Figure 3:
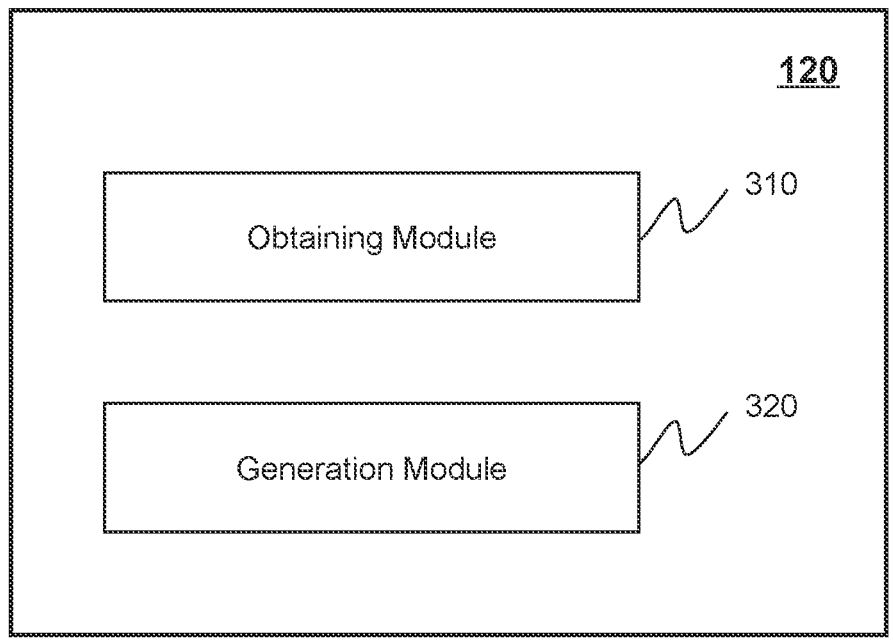
FIG. 3 is a block diagram illustrating an exemplary processing device according to some embodiments of the present disclosure.

FIG. 3 is a block diagram illustrating an exemplary processing device 120 according to some embodiments of the present disclosure. As shown in FIG. 3, the processing device 120 may include an obtaining module 310 and a generation module 320.

The obtaining module 310 may be configured to receive a parameter update instruction and receive an instruction to stop the parameter update instruction. More descriptions of the parameter update instruction and the instruction to stop the parameter update instruction may be found elsewhere in the present disclosure (e.g., operations 430 and 440, and the descriptions thereof).

The generation module 320 may be configured to generate ultrasound images of a target subject by performing an ultrasound imaging on the target subject. In some embodiments, the ultrasound imaging may at least include a first period and a second period following the first period, and the second period may be set by a parameter update instruction. An ultrasound image acquired in the first period may be generated using first compensation parameters. An ultrasound image acquired in the second period may be generated using second compensation parameters, wherein the second compensation parameters may be determined based on compensation parameters of the previous ultrasound image obtained immediately before the ultrasound image acquired in the second period. More descriptions of the first period and the second period may be found elsewhere in the present disclosure (e.g., FIG. 4 and the descriptions thereof).

In some embodiments, the generation module 320 may be configured to determine the second compensation parameters of the ultrasound image acquired in the second period by obtaining the previous ultrasound image and the compensation parameters of the previous ultrasound image; determining current compensation parameters by comparing pixel information of the previous ultrasound image and reference pixel information; and determining the second compensation parameters based on the compensation parameters of the previous ultrasound image and the current compensation parameters. More descriptions of the determination of the second compensation parameters may be found elsewhere in the present disclosure (e.g., FIG. 5 and the descriptions thereof).

In some embodiments, the generation module 320 may be configured to determine the pixel information of the previous ultrasound image by dividing the previous ultrasound image into multiple sub-image regions, the multiple sub-image regions corresponding to imaging positions having different distances with respect to an ultrasound probe configured to perform the ultrasound imaging; determining a median pixel value of each of the multiple sub-image regions; and determining the pixel information of the previous ultrasound image based on median pixel values corresponding to the multiple sub-image regions. More descriptions of the determination of the pixel information of the previous ultrasound image may be found elsewhere in the present disclosure (e.g., FIG. 6 and the descriptions thereof).

In some embodiments, the generation module 320 may be configured to determine the second compensation parameters based on the compensation parameters of the previous ultrasound image and the current compensation parameters by determining a degree of difference between the compensation parameters of the previous ultrasound image and the current compensation parameters; and determining the second compensation parameters based on a determination result of whether the degree of difference is smaller than or equal to a preset threshold. More descriptions of the determination of the second compensation parameters based on the compensation parameters of the previous ultrasound image and the current compensation parameters may be found elsewhere in the present disclosure (e.g., FIG. 7 and the descriptions thereof).

It should be noted that the above description is merely provided for the purposes of illustration, and not intended to limit the scope of the present disclosure. For persons having ordinary skills in the art, multiple variations and modifications may be made under the teachings of the present disclosure. However, those variations and modifications do not depart from the scope of the present disclosure. In some embodiments, the processing device 120 may include one or more additional modules, such as a storage module (not shown) for storing data.

The processing device 120 may generate ultrasound images of a target subject by performing an ultrasound imaging on the target subject. Specifically, the processing device 120 may cause an ultrasound imaging device (e.g., the ultrasound imaging device 110) to perform the ultrasound imaging. In the ultrasound imaging, an ultrasound probe (e.g., the ultrasonic probe 111) may emit ultrasonic waves to the target subject and receive ultrasound echo signals (also referred to as reflected ultrasonic waves). The processing device 120 may then generate the ultrasound images based on the ultrasound echo signals.

In some embodiments, the ultrasound imaging may at least include a first period and a second period following the first period, and the second period may be set by a parameter update instruction. An ultrasound image acquired in the first period may be generated using first compensation parameters. An ultrasound image acquired in the second period may be generated using second compensation parameters, wherein the second compensation parameters may be determined based on compensation parameters of the previous ultrasound image obtained immediately before the ultrasound image acquired in the second period. For the convenience of descriptions, an ultrasound image acquired in the first period is referred to as a first ultrasound image, and an ultrasound image acquired in the second period is referred to as a second ultrasound image.

Figure 4:
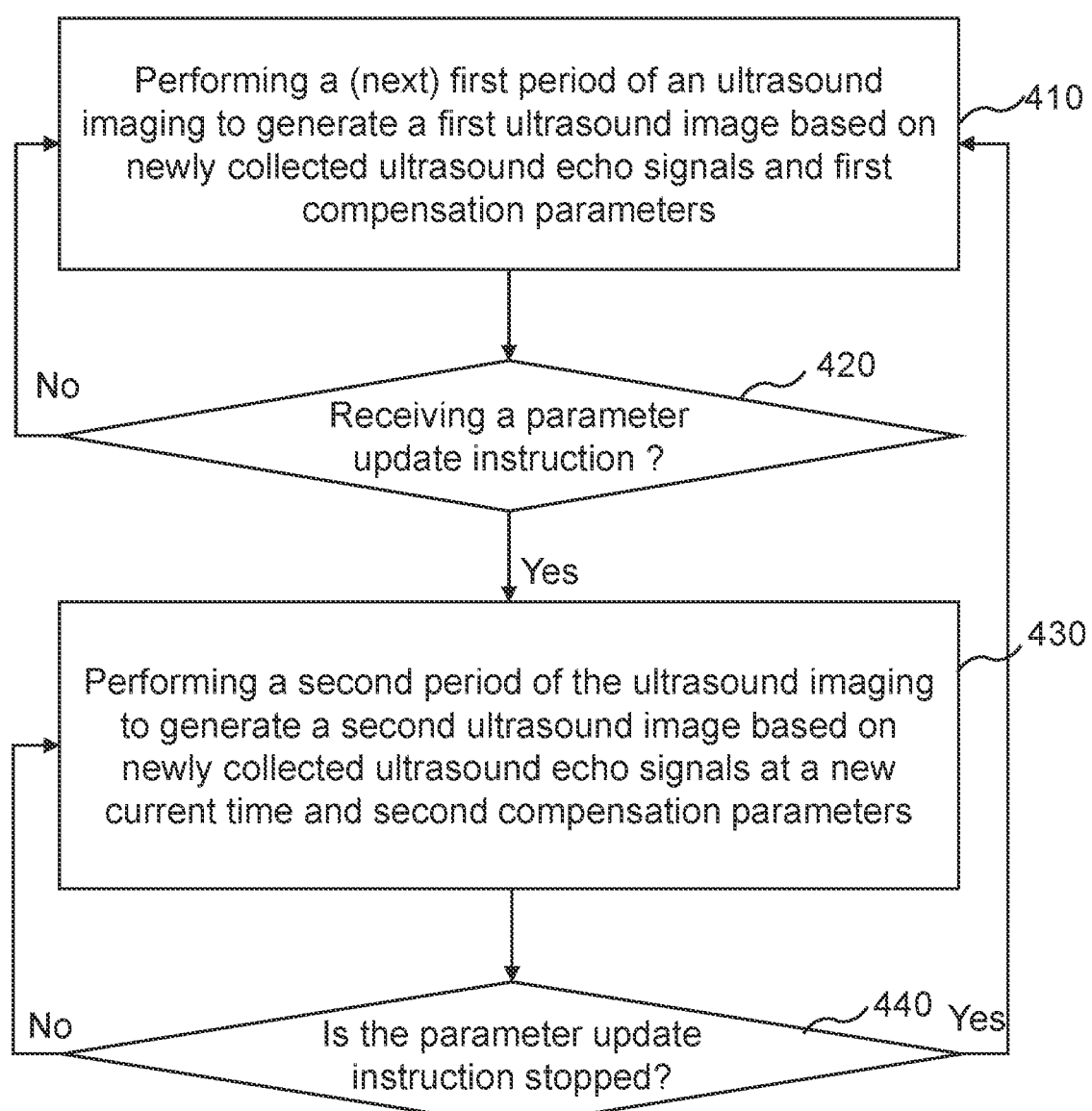
FIG. 4 is a flowchart illustrating an exemplary ultrasound imaging process according to some embodiments of the present disclosure.

For illustration purposes, FIG. 4 illustrates an exemplary ultrasound imaging process according to some embodiments of the present disclosure. In some embodiments, process 400 may be executed by the ultrasound imaging system 100. For example, the process 400 may be implemented as a set of instructions (e.g., an application) stored in a storage device (e.g., the storage device 130), and the processing device 120 (e.g., one or more modules illustrated in FIG. 3) may execute the set of instructions and may accordingly be directed to perform the process 400.

In 410, the processing device 120 (e.g., the generation module 320) may perform a first period of an ultrasound imaging to generate a first ultrasound image based on newly collected ultrasound echo signals and the first compensation parameters.

As used herein, a first period of an ultrasound imaging refers to a period of the ultrasound imaging performed before receiving a parameter update instruction.

The processing device 120 may obtain the newly collected ultrasound echo signals from the ultrasound imaging device via a network (e.g., the network 150). The newly collected ultrasound echo signals refer to ultrasound echo signals that have not been used to reconstruct ultrasound images.

In some embodiments, the ultrasound echo signals may be analog signals, and the processing device 120 may perform an analog time gain compensation (ATGC) on the ultrasound echo signals. For example, the processing device 120 may obtain gain compensation coefficients through a gain amplifier for amplifying or suppressing analog ultrasonic echo signals received by the ultrasonic probe. Further, the processing device 120 may multiply each of the ultrasound echo signals by its corresponding gain compensation coefficient. It should be noted that ATGC is optional, and subsequent beamforming may be performed on the ultrasound echo signals after or before ATGC.

In some embodiments, the processing device 120 (e.g., the generation module 320) may determine target signals (also referred to as digital ultrasonic echo signals) by performing beamforming on the ultrasound echo signals. In some embodiments, by the beamforming, the processing device 120 may realize signal processing for each of the ultrasonic echo signals. Merely by way of example, the signal processing may include signal extraction, signal analysis, data interpolation, or the like, or any combination thereof.

Further, the processing device 120 (e.g., the generation module 320) may generate the first ultrasound image based on the target signals and the first compensation parameters. The first compensation parameters may be preset according to system's default settings or by a user. In some embodiments, the first compensation parameters may include at least one of a digital time gain compensation (DTGC) parameter, a lateral gain compensation parameter, or a dynamic compression curve parameter of each target signal. Further, the processing device 120 may perform a DTGC on the target signals based on the first compensation parameters to determine processed target signals. For example, the processing device 120 may multiply each of the target signals by its corresponding first compensation parameter. Further, the processing device 120 may reconstruct the first ultrasound image based on the processed target signals using an image reconstruction method.

In 420, the processing device 120 (e.g., the obtaining module 310) may determine whether the parameter update instruction is received.

In some embodiments, the parameter update instruction may be inputted by a user (e.g., a doctor) via a user terminal. For example, the user may trigger the parameter update instruction by clicking or touching a corresponding key or position on the user terminal (e.g., a display, the terminal(s) 140). In some embodiments, the processing device 120 may automatically trigger the parameter update instruction by analyzing the first ultrasound image. For example, the processing device 120 may determine a uniformity of pixel values (e.g., grayscale values, brightness values) and determine whether to trigger the parameter update instruction based on a determination result of whether the uniformity of pixel values is less than a preset threshold (e.g., 10%, 20%, 30%). If the uniformity of pixel values is less than the preset threshold, the processing device 120 may trigger the parameter update instruction. If the uniformity of pixel values is not less than the preset threshold, the processing device 120 may not trigger the parameter update instruction.

In response to determining that the parameter update instruction is not received, the processing device 120 may proceed to operation 410 again to maintain the first period to generate a new first ultrasound image based on ultrasound echo signals collected at a new current time and the first compensation parameters.

In response to determining that the parameter update instruction is received, the processing device 120 may perform operation 430.

In 430, the processing device 120 (e.g., the generation module 320) may perform a second period of the ultrasound imaging to generate a second ultrasound image based on the newly collected ultrasound echo signals at the new current time and second compensation parameters.

As used herein, a second period of an ultrasound imaging refers to a period of the ultrasound imaging performed after receiving the parameter update instruction.

The processing device 120 may determine the second compensation parameters based on compensation parameters of the previous ultrasound image. The second compensation parameters may include DTGC parameters. Compensation parameters of an image refers to parameters used to generate the image. For example, the compensation parameters of the previous ultrasound image refers to parameters used to generate the previous ultrasound image. The previous ultrasound image refers to an ultrasound image obtained immediately before the current ultrasound image, that is, the current ultrasound image is obtained immediately following the previous ultrasound image. In some embodiments, the previous ultrasound image may be the last first ultrasound image acquired in the first period, and the compensation parameters of the previous ultrasound image may be the first compensation parameters of the last first ultrasound image. For example, when no other second ultrasound image was generated before this second ultrasound image, the previous ultrasound image may be the last first ultrasound image generated before the parameter update instruction is received, and the compensation parameters of the previous ultrasound image may be the first compensation parameters of the last first ultrasound image.

In some embodiments, the previous ultrasound image may be one second ultrasound image acquired in the second period, and the compensation parameters of the previous ultrasound image may be the second compensation parameters of the second ultrasound image. For example, when there are one or more other second ultrasound images generated before this second ultrasound image, the previous ultrasound image may be a previous second ultrasound image of this second ultrasound image, and the compensation parameters of the previous ultrasound image may be the second compensation parameters of the previous second ultrasound image. More descriptions of the determination of the second compensation parameters may be found elsewhere in the present disclosure (e.g., FIG. 5 and the descriptions thereof).

Further, the processing device 120 may generate the second ultrasound image based on the second compensation parameters and the newly collected ultrasound echo signals. Specifically, the processing device 120 may determine target signals by performing the beamforming on the newly collected ultrasound echo signals and perform the digital time gain compensation (DTGC) on the target signals based on the second compensation parameters to determine processed target signals. For example, the processing device 120 may multiply each of the target signals by its corresponding second compensation parameter. Further, the processing device 120 may generate the second ultrasound image based on the processed target signals. For example, the processing device 120 may reconstruct the second ultrasound image based on the processed target signals using an image reconstruction method.

In 440, the processing device 120 (e.g., the obtaining module 310) may determine whether the parameter update instruction is stopped. In some embodiments, the processing device 120 may receive a new instruction from the user to stop the parameter update instruction. In some embodiments, when the user may set a duration of the second period, and the processing device 120 may determine whether the parameter update instruction is stopped based on the duration.

In response to determining that the parameter update instruction is not stopped, the processing device 120 may proceed to operation 430 again to maintain the second period. Then, operation 430 may be performed again to generate a new second ultrasound image based on ultrasound echo signals collected at another new current time and second compensation parameters.

In response to determining that the parameter update instruction is stopped, the processing device 120 may proceed to operation 410 again to initiate a next first period of the ultrasound imaging. It should be noted that the process 400 would continue during the entire ultrasound imaging process until the end of the ultrasound imaging.

Conventionally, compensation parameter adjustment is performed intermittently in response to a user trigger command and always based on preset compensation parameters. For example, after receiving one user trigger command, the system executes compensation parameter adjustment based on the preset compensation parameters to determine new compensation parameters and executes TGC on the current frame using the determined compensation parameters. Then, the compensation parameter adjustment is stopped, and the system executes TGC using the preset compensation parameters for a next frame if no user trigger instruction is received; if the user trigger instruction is received again, the system needs to perform parameter adjustment again based on the preset compensation parameters to determine the compensation parameters of the next frame.

In the embodiments of the present disclosure, once the parameter update instruction is received, the processing device 120 would continuously maintain the second period of the ultrasound imaging to update the second compensation parameters of each second ultrasound image based on the compensation parameters of the previous ultrasound image until the parameter update instruction is stopped, which reduces user intervention and improves the accuracy of the second compensation parameters, thereby adaptively obtaining better image optimization results with fewer operations.

Figure 5:
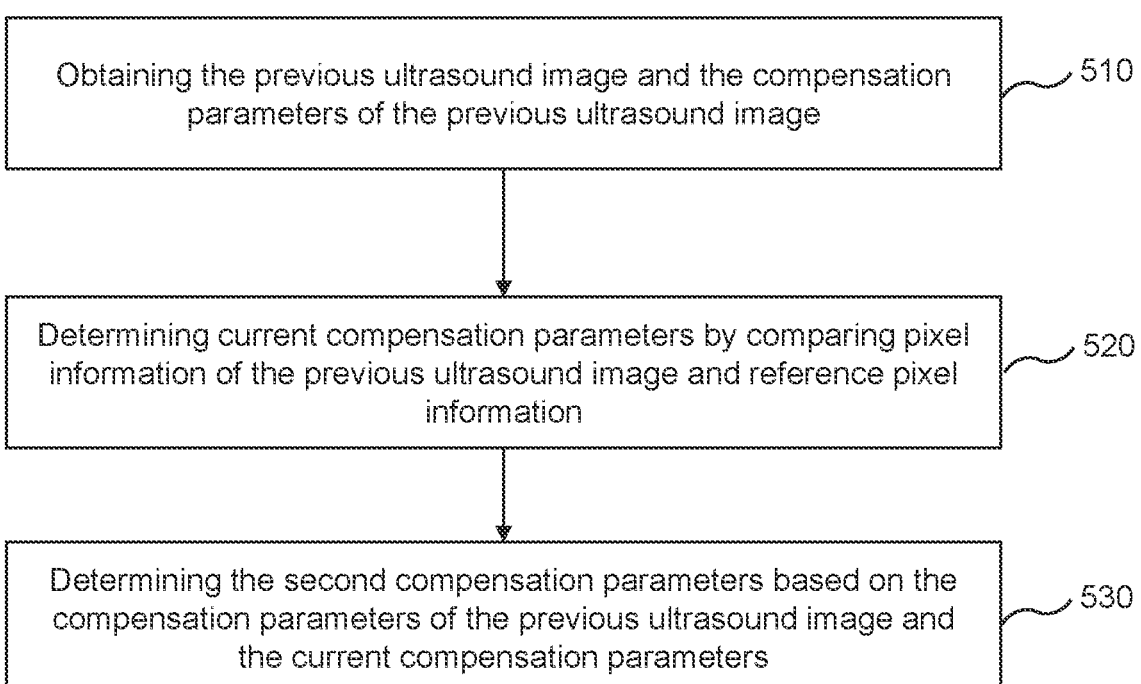
FIG. 5 is a flowchart illustrating an exemplary process for determining second compensation parameters used to generate a second ultrasound image according to some embodiments of the present disclosure.

FIG. 5 is a flowchart illustrating an exemplary process for determining second compensation parameters used to generate a second ultrasound image according to some embodiments of the present disclosure. In some embodiments, the process 500 may be performed to achieve at least part of operation 430 as described in connection with FIG. 4.

In 510, the processing device 120 (e.g., the generation module 320) may obtain a previous ultrasound image of the second ultrasound image and compensation parameters of the previous ultrasound image.

The previous ultrasound image refers to the latest ultrasound image generated before the process 500 is performed. As described in connection with FIG. 4, when no other second ultrasound image was generated before this second ultrasound image, the previous ultrasound image may be the last first ultrasound image generated before the parameter update instruction is received, and the compensation parameters of the previous ultrasound image may be the first compensation parameters of the last first ultrasound image; when there are one or more other second ultrasound images generated before this second ultrasound image, the previous ultrasound image may be a previous second ultrasound image of this second ultrasound image, and the compensation parameters of the previous ultrasound image may be the second compensation parameters of the previous second ultrasound image.

In 520, the processing device 120 (e.g., the generation module 320) may determine current compensation parameters by comparing pixel information of the previous ultrasound image and reference pixel information.

In some embodiments, the reference pixel information may include pixel information of an ideal image of the target subject acquired based on ideal compensation parameters. The ideal image may refer to an image whose uniformity of pixel values (e.g., grayscale values, brightness values) is greater than a preset threshold (e.g., 60%, 70%, 80%). Compensation parameters used to generate the ideal image are the ideal compensation parameters. Merely by way of example, pixel information of an image (e.g., the previous ultrasound image, the ideal image) may include pixel grayscale information, pixel brightness information, or the like, or any combination thereof. In some embodiments, the ideal image of the target subject may be acquired by performing a TGC (e.g., an ATGC and/or a DTGC) on ultrasound echo signals or target signals (determined by performing the beamforming on the ultrasound echo signals) of the target subject based on ideal compensation parameters (e.g., ATGC parameters and/or DTGC parameters). Different subjects may correspond to different ideal compensation parameters. The ideal compensation parameters corresponding to various objects may be previously determined by a user (e.g., a doctor) and stored in a storage device (e.g., the storage device 130, the storage 220) disclosed elsewhere in the present disclosure and/or an external storage device. The processing device 120 may obtain the ideal compensation parameters of the target subject from the storage device and/or the external storage device via a network (e.g., the network 150).

In some embodiments, the processing device 120 may determine the reference pixel information in a similar manner to the determination of the pixel information of the previous ultrasound image as described in connection with FIG. 6. For example, the processing device 120 may divide the ideal image into multiple regions. Further, the processing device 120 may determine a median pixel value of each of the multiple regions and determine the reference pixel information based on median pixel values corresponding to the regions.

In some embodiments, the processing device 120 may divide the previous ultrasound image into multiple sub-image regions. Further, the processing device 120 may determine a median pixel value of each of the multiple sub-image regions and determine the pixel information of the previous ultrasound image based on median pixel values corresponding to the multiple sub-image regions. More descriptions of the determination of the pixel information of the previous ultrasound image may be found elsewhere in the present disclosure (e.g., FIG. 6 and the descriptions thereof).

In some embodiments, the processing device 120 may determine the current compensation parameters by comparing the pixel information of the previous ultrasound image and the reference pixel information according to formula (1) below:

$$C_{curr_i} = \frac{G_{pre_i}}{G_{ideal_i}},$$ (1)

where $C_{curr_i}$ refers to a current compensation parameter corresponding to an i-th sub-image region, $G_{pre_i}$ refers to pixel information of the previous ultrasound image corresponding to the i-th sub-image region, and $G_{ideal_i}$ refers to reference pixel information corresponding to the i-th sub-image region. In some embodiments, when there are n sub-image regions, $C_{curr_i}$ to $C_{curr_n}$ may be represented as a curve or a function representing the current compensation parameters corresponding to the n sub-image regions, $G_{pre_1}$ to $G_{pre_n}$ may be represented as a curve or a function representing the pixel information of the previous ultrasound image corresponding to the n sub-image regions, and $G_{ideal_1}$ to $G_{ideal_n}$ may be represented as a curve or a function representing the reference pixel information corresponding to the n sub-image regions. More descriptions of the curve or function may be found elsewhere in the present disclosure (e.g., FIG. 6 and the descriptions thereof).

In 520, the processing device 120 (e.g., the generation module 320) may determine the second compensation parameters based on the compensation parameters of the previous ultrasound image and the current compensation parameters.

In some embodiments, the processing device 120 may determine a degree of difference between the compensation parameters of the previous ultrasound image and the current compensation parameters, and determine the second compensation parameters based on a determination result of whether the degree of difference is smaller than or equal to a preset threshold. More descriptions of the determination of the second compensation parameters based on the compensation parameters of the previous ultrasound image and the current compensation parameters may be found elsewhere in the present disclosure (e.g., FIG. 7 and the descriptions thereof).

In some embodiments, the processing device 120 may generate the second ultrasound image based on the second compensation parameters. For example, for each sub-image region, the processing device 120 may perform the DTGC on target signals of the second ultrasound image corresponding to the sub-image region based on a second compensation parameter corresponding to the sub-image region, so that the DTGC may be performed on different sub-image regions based on different second compensation parameters, thereby improving the accuracy of the DTGC for the second ultrasonic image, and accordingly, improving the image quality (e.g., relatively consistent in brightness and/or grayscale) of the generated second ultrasonic image.

In the embodiments of the present disclosure, the current compensation parameters are determined by comparing the pixel information of the previous ultrasound image and the reference pixel information, and then the second ultrasound image is generated based on the second compensation parameters that are determined based on the current compensation parameters, so that the uniformity of pixel values (e.g., grayscale values, brightness values) in the generated second ultrasound image may be closer to the ideal image than the previous ultrasound image, thereby improving the quality of the generated second image.

Figure 6:
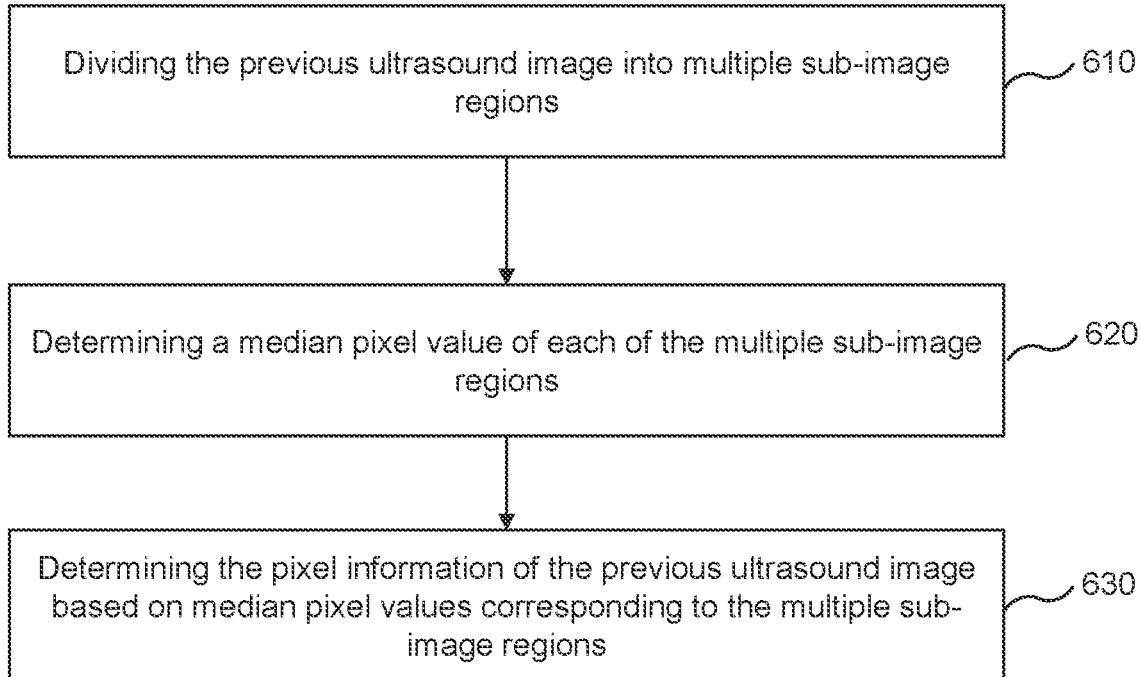
FIG. 6 is a flowchart illustrating an exemplary process for determining pixel information of a previous ultrasound image according to some embodiments of the present disclosure.

FIG. 6 is a flowchart illustrating an exemplary process for determining pixel information of a previous ultrasound image according to some embodiments of the present disclosure. In some embodiments, the process 600 may be performed to achieve at least part of operation 520 as described in connection with FIG. 5.

In 610, the processing device 120 (e.g., the generation module 320) may divide the previous ultrasound image into multiple sub-image regions.

In some embodiments, the multiple sub-image regions may correspond to imaging positions having different distances (also referred to as imaging depths) with respect to an ultrasound probe (e.g., the ultrasonic probe 111 illustrated in FIG. 1) configured to perform an ultrasound imaging. For example, the processing device 120 may divide the previous ultrasound image into the multiple sub-image regions based on the distances between the imaging positions of the target subject and the ultrasound probe. Specifically, the distances between the imaging positions of the target subject and the ultrasound probe may be in a range (e.g., 0-10 mm). The processing device 120 may divide the range into a preset number of subranges (e.g., 5 subranges, 10 subranges) and divide the previous ultrasound image based on the preset number of subranges. Each of the multiple sub-image regions may correspond to imaging positions having distances in one subrange.

In 620, the processing device 120 (e.g., the generation module 320) may determine a median pixel value of each of the multiple sub-image regions.

In some embodiments, pixel values of each sub-image region may include grayscale values, brightness values, or the like, or any combination thereof.

In 630, the processing device 120 (e.g., the generation module 320) may determine the pixel information of the previous ultrasound image based on median pixel values corresponding to the multiple sub-image regions.

In some embodiments, the processing device 120 may designate the median pixel values corresponding to the multiple sub-image regions as the pixel information of the previous ultrasound image. In some alternative embodiment, the processing device 120 may determine the pixel information of the previous ultrasound image by processing the median pixel values corresponding to the multiple sub-image regions. For example, the pixel information of the previous ultrasound image may be represented by a curve indicating a relationship between the median pixel value and the distance of each of the multiple sub-image regions. For example, the ordinate of the curve is the median pixel value and the abscissa of the curve is the distance (i.e., the imaging depth). The processing device 120 may determine the curve representing the pixel information of the previous ultrasound image by fitting the median pixel values corresponding to the multiple sub-image regions. In such cases, the second compensation parameters determined based on the pixel information of the previous ultrasound image may be represented by a curve indicating a relationship between the digital time gain compensation (DTGC) parameters and imaging depths. In some embodiments, the curve representing the pixel information of the previous ultrasound image may be represented by a function. In such cases, the curve representing the second compensation parameters may also be represented by a function.

Typically, the pixel information of an ultrasound image may be determined by determining an arithmetic mean or a weighted mean of pixel values of each sub-image region. However, for a sub-image region with obvious tissue differences (e.g., a sub-image region that includes both highdensity tissue and low-density tissue), the arithmetic mean is difficult to represent a gain level of the sub-image region, and the determination of weights of pixel values used to determine the weighted mean requires certain experience and professional knowledge. In the present disclosure, the pixel information of the previous ultrasound image may be determined by determining median pixel values corresponding to the multiple sub-image regions, which may eliminate the influence of some maximum and minimum pixel values, thereby improving the accuracy of the determined pixel information of the previous ultrasound image, and accordingly, improving the accuracy of the current compensation parameters determined based on the pixel information.

Figure 7:
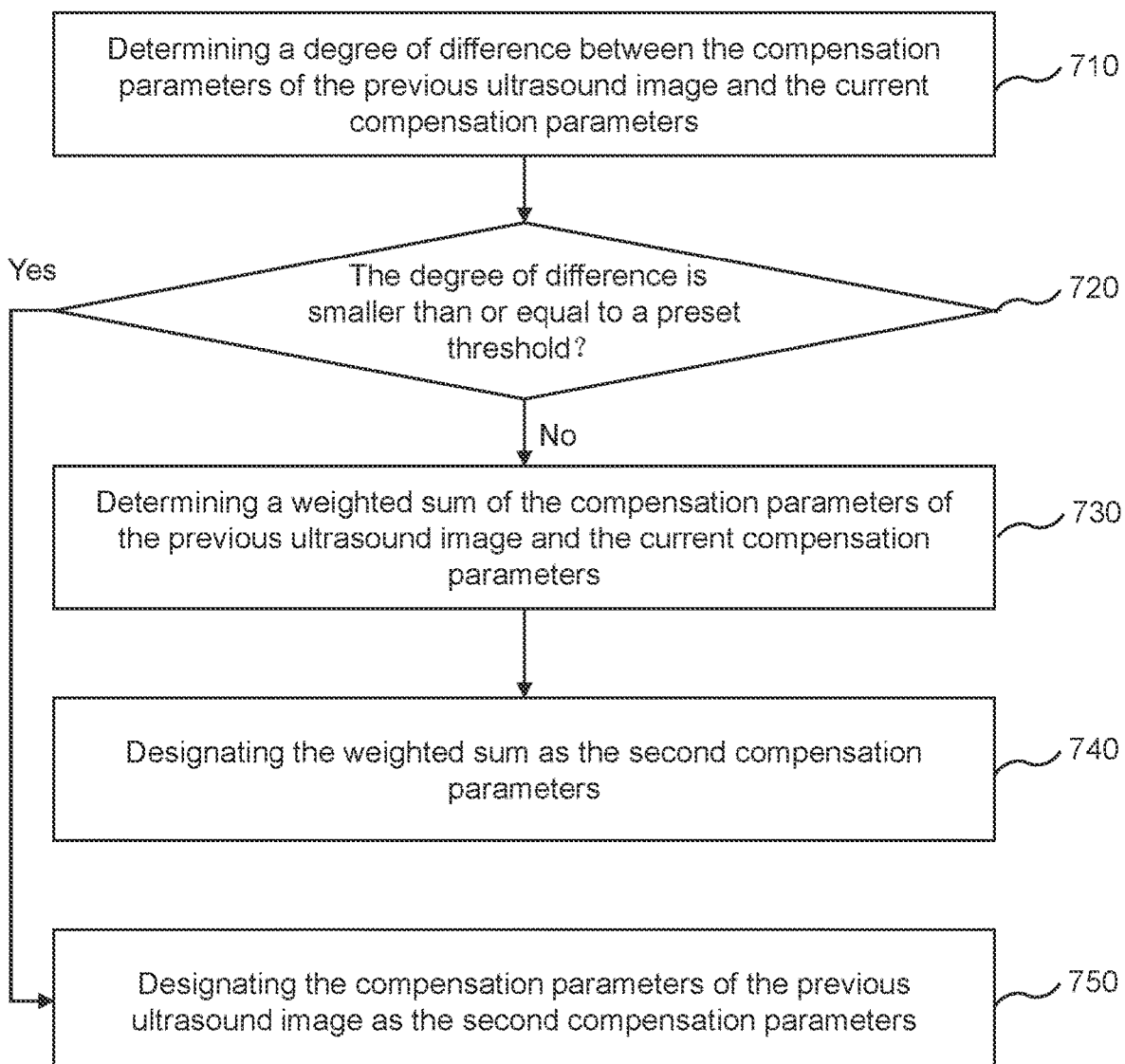
FIG. 7 is a flowchart illustrating an exemplary process for determining second compensation parameters according to some embodiments of the present disclosure.

FIG. 7 is a flowchart illustrating an exemplary process for determining second compensation parameters according to some embodiments of the present disclosure. In some embodiments, the process 700 may be performed to achieve at least part of operation 530 as described in connection with FIG. 5.

In 710, the processing device 120 (e.g., the generation module 320) may determine a degree of difference between compensation parameters of a previous ultrasound image and current compensation parameters.

In some embodiments, the processing device 120 may determine the degree of difference between the compensation parameters of the previous ultrasound image and the current compensation parameters by comparing the compensation parameters of the previous ultrasound image and the current compensation parameters. For example, the processing device 120 may determine the degree of difference by comparing the curve representing the compensation parameters of the previous ultrasound image and the curve representing the current compensation parameters.

In some embodiments, the degree of difference may be a mean square error of the compensation parameters of the previous ultrasound image and the current compensation parameters. In some embodiments, the processing device 120 may determine the mean square error of the compensation parameters of the previous ultrasound image and the current compensation parameters according to formula (2) below:

$$D = \sqrt{\frac{1}{n}\sum_{i=1}^{n}\left(C_{curr_i} - C_{pre_i}\right)^2}, \qquad (2)$$

where D refers to the mean square error of the compensation parameters of the previous ultrasound image and the current compensation parameters, n refers to a count of the multiple sub-image regions (that is a count of the compensation parameters of the previous ultrasound image or a count of the current compensation parameters), $C_{pre_i}$ refers to a compensation parameter of the previous ultrasound image corresponding to an i-th sub-image region, and $C_{curr_i}$ refers to a current compensation parameter corresponding to the i-th sub-image region.

In 720, the processing device 120 (e.g., the generation module 320) may whether the degree of difference is smaller than or equal to a preset threshold.

In some embodiments, the preset threshold may affect a compensation parameter update frequency in the second period of the ultrasound imaging. A high compensation parameter update frequency may cause the image brightness or grayscale to change too quickly, thereby reducing image stability. A low compensation parameter update frequency may lead to sudden changes in image brightness or grayscale, thereby degrading image quality. Therefore, the preset threshold may be set to achieve an appropriate compensation parameter update frequency. For example, the preset threshold may be in a range of 2%-10% (e.g., 3%, 5%, 7%). In response to determining that the degree of difference is larger than the preset threshold, the processing device 120 may perform operation 730. In response to determining that the degree of difference is smaller than or equal to the preset threshold, the processing device 120 may perform operation 750.

In 730, the processing device 120 (e.g., the generation module 320) may determine a weighted sum of the compensation parameters of the previous ultrasound image and the current compensation parameters.

In some embodiments, weights of the compensation parameters of the previous ultrasound image and the current compensation parameters are determined based on the degree of difference. Compared with the compensation parameters of the previous ultrasound image, the current compensation parameters determined based on the pixel information of the previous ultrasound image and reference pixel information are more suitable for generating the current second ultrasound image. The greater the degree of difference, the more suitable the current compensation parameters are for generating the current second ultrasound image, and thus the greater the weight of the current compensation parameters. In this way, the determined second compensation parameters may be more suitable for generating the current second ultrasound image, and accordingly, the greater the uniformity of pixel values (e.g., grayscale values, brightness values) in the generated second ultrasound image. In some embodiments, a sum of the weights of the compensation parameters of the previous ultrasound image and the current compensation parameters may be equal to 1.

In some embodiments, the processing device 120 may determine the weighted sum of the compensation parameters of the previous ultrasound image and the current compensation parameters according to formula (3) below:

$$S_i = aC_{curr_i} + bC_{pre_i}, \qquad (3)$$

where $S_i$ refers to a weighted sum corresponding to an i-th sub-image region, $C_{curr_i}$ refers to a current compensation parameter corresponding to the i-th sub-image region, $C_{pre_i}$ refers to a compensation parameter of the previous ultrasound image corresponding to the i-th sub-image region, and a and b refer to weights of the compensation parameters of the previous ultrasound image and the current compensation parameters corresponding to all sub-image regions, respectively. In some embodiments, when there are n sub-image regions, $S_1$ to $S_n$ refers to a curve or a function representing the weighted sum corresponding to the n sub-image regions, $C_{curr_i}$ to $C_{curr_n}$ refers to a curve or a function representing the current compensation parameters corresponding to the n sub-image regions, $C_{pre_i}$ to $C_{pre_n}$ refers to a curve or a function representing the compensation parameters of the previous ultrasound image corresponding to the n sub-image regions, and a and b refers to weights of the $C_{curr_i}$ and the $C_{pre_i}$, respectively.

In 740, the processing device 120 (e.g., the generation module 320) may designate the weighted sum as the second compensation parameters.

In 750, the processing device 120 (e.g., the generation module 320) may designate the compensation parameters of the previous ultrasound image as the second compensation parameters.

In the embodiments of the present disclosure, the second compensation parameters are determined based on a determination result of whether the degree of difference is smaller than or equal to the preset threshold. Since the preset threshold may affect the compensation parameter update frequency in the second period of the ultrasound imaging, by setting an appropriate preset threshold (e.g., in a range of 2%-10%), an appropriate compensation parameter update frequency may be achieved, thereby improving the image stability and the image quality (e.g., relatively consistent in brightness and/or grayscale).

Figure 8:
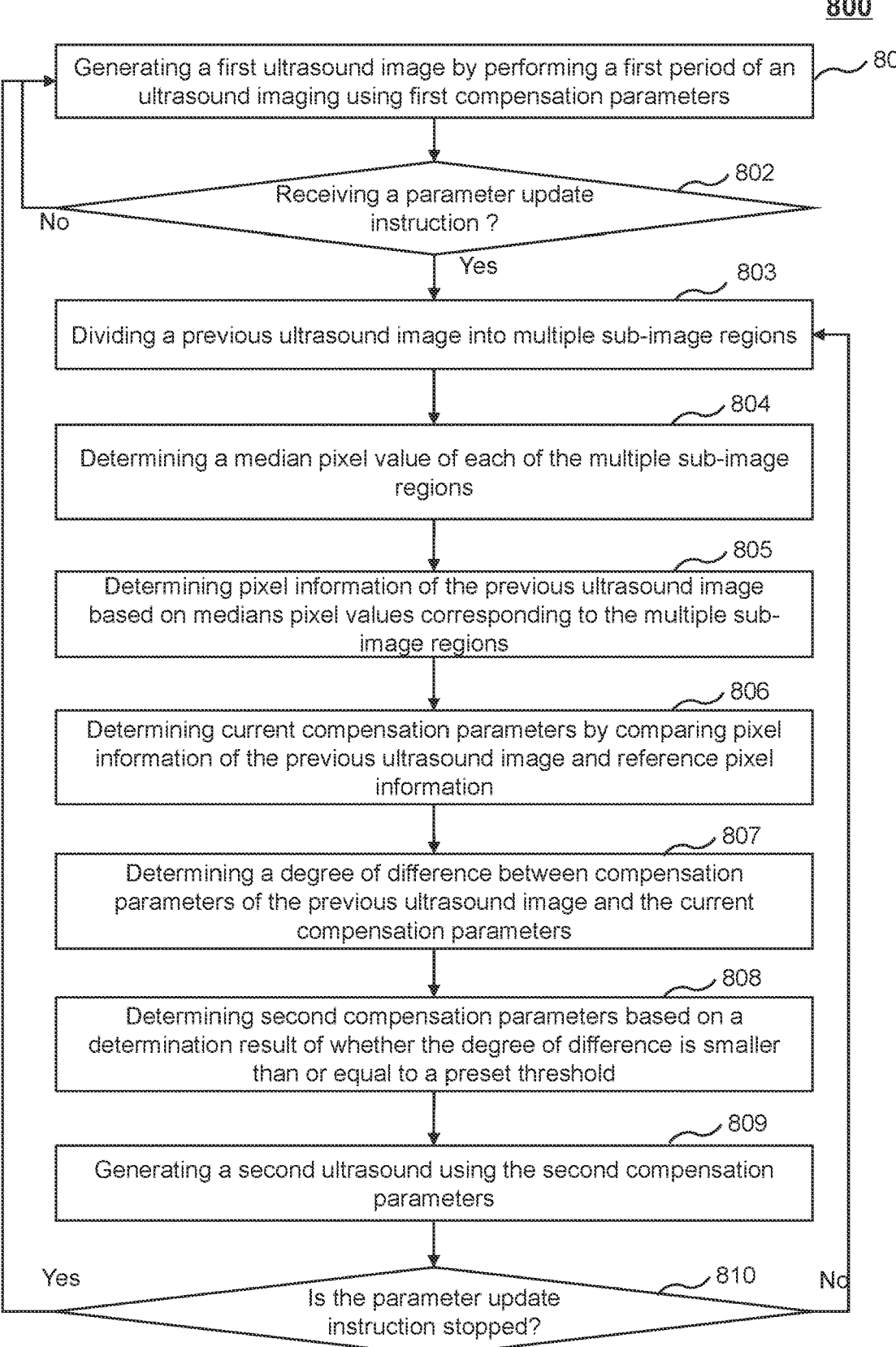
FIG. 8 is a flowchart illustrating an exemplary ultrasound imaging process according to some embodiments of the present disclosure.

FIG. 8 is a flowchart illustrating an exemplary ultrasound imaging process according to some embodiments of the present disclosure. In some embodiments, process 800 may be executed by the ultrasound imaging system 100. For example, the process 800 may be implemented as a set of instructions (e.g., an application) stored in a storage device (e.g., the storage device 130). In some embodiments, the processing device 120 (e.g., one or more modules illustrated in FIG. 3) may execute the set of instructions and may accordingly be directed to perform the process 800.

In 801, the processing device 120 (e.g., the generation module 320) may generate a first ultrasound image by performing a first period of an ultrasound imaging using first compensation parameters. Operation 801 may be performed in a similar manner to operations 410 as described in connection with FIG. 4.

In 802, the processing device 120 (e.g., the obtaining module 310) may determine whether a parameter update instruction is received. In response to determining that the parameter update instruction is received, the processing device 120 may perform operations 803-809 to generate a second ultrasound image by performing a second period of the ultrasound imaging. In response to determining that the parameter update instruction is not received, the processing device 120 may perform operation 801 again to generate a next first ultrasound image until the parameter update instruction is received. Operation 802 may be performed in a similar manner to operation 420 as described in connection with FIG. 4.

In 803, the processing device 120 (e.g., the generation module 320) may divide a previous ultrasound image into multiple sub-image regions. When no other second ultrasound image was generated before operation 803, the previous ultrasound image may be the last first ultrasound image generated before the parameter update instruction is received; when there are one or more other second ultrasound images generated before operation 803, the previous ultrasound image may be a previous second ultrasound image. Operation 803 may be performed in a similar manner to operation 610 as described in connection with FIG. 6.

In 804, the processing device 120 (e.g., the generation module 320) may determine a median pixel value of each of the multiple sub-image regions. Operation 804 may be performed in a similar manner to operation 620 as described in connection with FIG. 6.

In 805, the processing device 120 (e.g., the generation module 320) may determine the pixel information of the previous ultrasound image based on median pixel values corresponding to the multiple sub-image regions. Operation 805 may be performed in a similar manner to operation 630 as described in connection with FIG. 6.

In 806, the processing device 120 (e.g., the generation module 320) may determine current compensation parameters by comparing pixel information of the previous ultrasound image and reference pixel information. Operation 806 may be performed in a similar manner to operation 520 as described in connection with FIG. 5.

In 807, the processing device 120 (e.g., the generation module 320) may determine a degree of difference between compensation parameters of a previous ultrasound image and current compensation parameters. Operation 807 may be performed in a similar manner to operation 710 as described in connection with FIG. 7.

In 808, the processing device 120 (e.g., the generation module 320) may determine second compensation parameters based on a determination result of whether the degree of difference is smaller than or equal to a preset threshold. Operation 808 may be performed in a similar manner to operations 720-740 as described in connection with FIG. 7.

In 809, the processing device 120 (e.g., the generation module 320) may generate a second ultrasound image using the second compensation parameters. Operation 809 may be performed in a similar manner to operation 430 as described in connection with FIG. 4.

In 810, the processing device 120 (e.g., the obtaining module 310) may determine whether the parameter update instruction is stopped. In response to determining that the parameter update instruction is not stopped, the processing device 120 may perform operations 803-809 again to generate a next second ultrasound image until the parameter update instruction is stopped. In response to determining that the parameter update instruction is stopped, the processing device 120 may perform operation 801 to generate a next first ultrasound image until receiving a next parameter update instruction. Operation 810 may be performed in a similar manner to operation 440 as described in connection with FIG. 4.

The operations of the illustrated processes 400, 500, 600, 700, and 800 presented above are intended to be illustrative. In some embodiments, a process may be accomplished with one or more additional operations not described, and/or without one or more of the operations discussed. Additionally, the order in which the operations of a process described above is not intended to be limiting.

Having thus described the basic concepts, it may be rather apparent to those skilled in the art after reading this detailed disclosure that the foregoing detailed disclosure is intended to be presented by way of example only and is not limiting. Various alterations, improvements, and modifications may occur and are intended to those skilled in the art, though not expressly stated herein. These alterations, improvements, and modifications are intended to be suggested by this disclosure, and are within the spirit and scope of the exemplary embodiments of this disclosure.

Moreover, certain terminology has been used to describe embodiments of the present disclosure. For example, the terms "one embodiment," "an embodiment," and/or "some embodiments" may mean that a particular feature, structure or characteristic described in connection with the embodiment is included in at least one embodiment of the present disclosure. Therefore, it is emphasized and should be appreciated that two or more references to "an embodiment" or "one embodiment" or "an alternative embodiment" in various portions of this specification are not necessarily all referring to the same embodiment. Furthermore, the particular features, structures or characteristics may be combined as suitable in one or more embodiments of the present disclosure.

Further, it will be appreciated by one skilled in the art, aspects of the present disclosure may be illustrated and described herein in any of a number of patentable classes or context including any new and useful process, machine, manufacture, or composition of matter, or any new and useful improvement thereof. Accordingly, aspects of the present disclosure may be implemented entirely hardware, entirely software (including firmware, resident software, micro-code, etc.) or combining software and hardware implementation that may all generally be referred to herein as a "unit," "module," or "system." Furthermore, aspects of the present disclosure may take the form of a computer program product embodied in one or more computer readable media having computer readable program code embodied thereon.

A computer readable signal medium may include a propagated data signal with computer readable program code embodied therein, for example, in baseband or as part of carrier wave. Such a propagated signal may take any of a variety of forms, including electro-magnetic, optical, or the like, or any suitable combination thereof. A computer readable signal medium may be any computer readable medium that is not a computer readable storage medium and that may communicate, propagate, or transport a program for use by or in connection with an instruction execution system, apparatus, or device. Program code embodied on a computer readable signal medium may be transmitted using any appropriate medium, including wireless, wireline, optical fiber cable, RF, or the like, or any suitable combination of the foregoing.

Computer program code for carrying out operations for aspects of the present disclosure may be written in any combination of one or more programming languages, including an object oriented programming language such as Java, Scala, Smalltalk, Eiffel, JADE, Emerald, C++, C#, VB. NET, Python or the like, conventional procedural programming languages, such as the "C" programming language, Visual Basic, Fortran 2103, Perl, COBOL 2102, PHP, ABAP, dynamic programming languages such as Python, Ruby and Groovy, or other programming languages. The program code may execute entirely on the user's computer, partly on the user's computer, as a stand-alone software package, partly on the user's computer and partly on a remote computer or entirely on the remote computer or server. In the latter scenario, the remote computer may be connected to the user's computer through any type of network, including a local area network (LAN) or a wide area network (WAN), or the connection may be made to an external computer (for example, through the Internet using an Internet Service Provider) or in a cloud computing environment or offered as a service such as a Software as a Service (SaaS).

Furthermore, the recited order of processing elements or sequences, or the use of numbers, letters, or other designations therefore, is not intended to limit the claimed processes and methods to any order except as may be specified in the claims. Although the above disclosure discusses through various examples what is currently considered to be a variety of useful embodiments of the disclosure, it is to be understood that such detail is solely for that purpose, and that the appended claims are not limited to the disclosed embodiments, but, on the contrary, are intended to cover modifications and equivalent arrangements that are within the spirit and scope of the disclosed embodiments. For example, although the implementation of various components described above may be embodied in a hardware device, it may also be implemented as a software only solution, for example, an installation on an existing server or mobile device.

Similarly, it should be appreciated that in the foregoing description of embodiments of the present disclosure, various features are sometimes grouped together in a single embodiment, figure, or description thereof for the purpose of streamlining the disclosure aiding in the understanding of one or more of the various inventive embodiments. This method of disclosure, however, is not to be interpreted as reflecting an intention that the claimed object matter requires more features than are expressly recited in each claim. Rather, inventive embodiments lie in less than all features of a single foregoing disclosed embodiment.

In some embodiments, the numbers expressing quantities or properties used to describe and claim certain embodiments of the application are to be understood as being modified in some instances by the term "about," "approximate," or "substantially." For example, "about," "approximate," or "substantially" may indicate ±1%, ±5%, ±10%, or ±20% variation of the value it describes, unless otherwise stated. Accordingly, in some embodiments, the numerical parameters set forth in the written description and attached claims are approximations that may vary depending upon the desired properties sought to be obtained by a particular embodiment. In some embodiments, the numerical parameters should be construed in light of the number of reported significant digits and by applying ordinary rounding techniques. Notwithstanding that the numerical ranges and parameters setting forth the broad scope of some embodiments of the application are approximations, the numerical values set forth in the specific examples are reported as precisely as practicable.

Each of the patents, patent applications, publications of patent applications, and other material, such as articles, books, specifications, publications, documents, things, and/or the like, referenced herein is hereby incorporated herein by this reference in its entirety for all purposes, excepting any prosecution file history associated with same, any of same that is inconsistent with or in conflict with the present document, or any of same that may have a limiting effect as to the broadest scope of the claims now or later associated with the present document. By way of example, should there be any inconsistency or conflict between the description, definition, and/or the use of a term associated with any of the incorporated material and that associated with the present document, the description, definition, and/or the use of the term in the present document shall prevail.

In closing, it is to be understood that the embodiments of the application disclosed herein are illustrative of the principles of the embodiments of the application. Other modifications that may be employed may be within the scope of the application. Thus, by way of example, but not of limitation, alternative configurations of the embodiments of the application may be utilized in accordance with the teachings herein. Accordingly, embodiments of the present application are not limited to that precisely as shown and described.

What is claimed is:

1. A method for ultrasound imaging, implemented on a computing device including at least one processor and at least one storage device, the method comprising:

generating ultrasound images of a target subject by performing an ultrasound imaging on the target subject, wherein the ultrasound imaging at least includes a first period and a second period following the first period, the second period being initiated by a compensation parameter update instruction, the compensation parameter update instruction being triggered by a user on a user terminal, all first ultrasound images acquired in the first period are generated using first compensation parameters, and a second ultrasound image acquired in the second period is generated using second compensation parameters, the second compensation parameters being determined based on compensation parameters of a previous ultrasound image, wherein when no other second ultrasound image was generated before the second ultrasound image, the previous ultrasound image is a last first ultrasound image generated before the compensation parameter update instruction is received, and the compensation parameters of the previous ultrasound image are first compensation parameters of the last first ultrasound image, and when there are one or more other second ultrasound images generated before the second ultrasound image, the previous ultrasound image is a previous second ultrasound image of the second ultrasound image, and the compensation parameters of the previous ultrasound image are second compensation parameters of the previous second ultrasound image.

2. The method of claim 1, wherein for the second ultrasound image acquired in the second period, the corresponding second compensation parameters are determined by:

obtaining the previous ultrasound image and the compensation parameters of the previous ultrasound image;

determining current compensation parameters by comparing pixel information of the previous ultrasound image and reference pixel information; and determining the second compensation parameters based on the compensation parameters of the previous ultrasound image and the current compensation parameters.

3. The method of claim 2, wherein the reference pixel information includes pixel information of an ideal image of the target subject acquired based on ideal compensation parameters.

4. The method of claim 2, wherein the pixel information of the previous ultrasound image is determined by:

dividing the previous ultrasound image into multiple sub-image regions;

determining a median pixel value of each of the multiple sub-image regions; and determining the pixel information of the previous ultrasound image based on median pixel values corresponding to the multiple sub-image regions.

5. The method of claim 2, wherein the determining the second compensation parameters based on the compensation parameters of the previous ultrasound image and the current compensation parameters includes:

determining a degree of difference between the compensation parameters of the previous ultrasound image and the current compensation parameters; and determining the second compensation parameters based on a determination result of whether the degree of difference is smaller than or equal to a preset threshold.

6. The method of claim 5, wherein the degree of difference is a mean square error of the compensation parameters of the previous ultrasound image and the current compensation parameters.

7. The method of claim 5, wherein the determination result includes that the degree of difference is smaller than or equal to the preset threshold, and the determining the second compensation parameters includes designating the compensation parameters of the previous ultrasound image as the second compensation parameters.

8. The method of claim 5, wherein the determination result includes that the degree of difference is larger than the preset threshold, and the determining the second compensation parameters includes determining a weighted sum of the compensation parameters of the previous ultrasound image and the current compensation parameters, and designating the weighted sum as the second compensation parameters.

9. The method of claim 8, wherein weights of the compensation parameters of the previous ultrasound image and the current compensation parameters are determined based on the degree of difference, and the greater the degree of difference, the more suitable the current compensation parameters are for generating the second ultrasound image acquired in the second period, and thus the greater the weight of the current compensation parameters.

10. The method of claim 1, wherein the second period of the ultrasound imaging is performed by:

in response to determining that the compensation parameter update instruction is received, obtaining the previous ultrasound image and the compensation parameters of the previous ultrasound image;

determining current compensation parameters by comparing pixel information of the previous ultrasound image and reference pixel information;

determining the second compensation parameters based on the compensation parameters of the previous ultrasound image and the current compensation parameters;

generating the second ultrasound image acquired in the second period using the second compensation parameters; and designating the second ultrasound image acquired in the second period and the second compensation parameters as the previous ultrasound image and the compensation parameters of the previous ultrasound image to perform a next second period until the compensation parameter update instruction is stopped.

11. The method of claim 10, wherein the method further includes:

in response to determining that the compensation parameter update instruction is stopped, initiating a next first period of the ultrasound imaging to obtain the first compensation parameters and generate a next first ultrasound image acquired in the next first period using the first compensation parameters.

12. The method of claim 1, wherein the first compensation parameters and the second compensation parameters are digital time gain compensation (DTGC) parameters, and the second compensation parameters are represented by a curve or a function indicating a relationship between the digital time gain compensation (DTGC) parameters and imaging depths.

13. An ultrasound imaging system, comprising:

an ultrasound imaging device;

at least one storage device including a set of instructions; and at least one processor in communication with the at least one storage device, wherein when executing the set of instructions, the at least one processor causes the system to perform operations including:

generating ultrasound images of a target subject by causing the ultrasound imaging device to perform an ultrasound imaging on the target subject, wherein the ultrasound imaging at least includes a first period and a second period following the first period, the second period being initiated by a compensation parameter update instruction, and the compensation parameter update instruction being triggered by a user on a user terminal, all first ultrasound images acquired in the first period are generated using first compensation parameters, a second ultrasound image acquired in the second period is generated using second compensation parameters, the second compensation parameters being determined based on compensation parameters of a previous ultrasound image, and after the second period is initiated by the compensation parameter update instruction, the second period includes:

determining whether a degree of difference between the compensation parameters of the previous ultrasound image and current compensation parameters is smaller than or equal to a preset threshold; and performing automatic compensation parameter adjustment based on a determination result of whether the degree of difference is smaller than or equal to a preset threshold.

14. A method for ultrasound imaging, implemented on a computing device including at least one processor and at least one storage device, the method comprising:

in response to determining that a compensation parameter update instruction is received, obtaining a previous ultrasound image and compensation parameters of the previous ultrasound image, the compensation parameter update instruction being triggered by a user on a user terminal;

determining second compensation parameters based on the compensation parameters of the previous ultrasound image;

generating a second ultrasound image using the second compensation parameters; and designating the second ultrasound image and the second compensation parameters as the previous ultrasound image and the compensation parameters of the previous ultrasound image to determine next second compensation parameters and generate a next second ultrasound image until the compensation parameter update instruction is stopped, wherein when no other second ultrasound image was generated before the second ultrasound image, the previous ultrasound image is a last first ultrasound image generated before the compensation parameter update instruction is received, and the compensation parameters of the previous ultrasound image are first compensation parameters of the last first ultrasound image, and when there are one or more other second ultrasound images generated before the second ultrasound image, the previous ultrasound image is a previous second ultrasound image of the second ultrasound image, and the compensation parameters of the previous ultrasound image are second compensation parameters of the previous second ultrasound image.

15. The method of claim 2, wherein the current compensation parameters are determined according to a formula below:

$$C_{curr_i} = \frac{G_{pre_i}}{G_{ideal_i}},$$

where $C_{curr_i}$ refers to a current compensation parameter corresponding to an i-th sub-image region of the previous ultrasound image, $G_{pre_i}$ refers to pixel information of the previous ultrasound image corresponding to the i-th sub-image region, and $G_{ideal_i}$ refers to reference pixel information corresponding to the i-th sub-image region.

16. The method of claim 15, wherein after the second period is initiated by the compensation parameter update instruction, the method further includes:

determining whether a degree of difference between the compensation parameters of the previous ultrasound image and the current compensation parameters is smaller than or equal to a preset threshold; and performing automatic compensation parameter adjustment based on a determination result of whether the degree of difference is smaller than or equal to a preset threshold.

17. The method of claim 16, wherein when there are n sub-image regions in the previous ultrasound image, $C_{curr_1}$ to $C_{curr_n}$ is represented as a curve or a function representing the current compensation parameters corresponding to the n sub-image regions, $G_{pre_1}$ to $G_{pre_n}$ is represented as a curve or a function representing the pixel information of the previous ultrasound image corresponding to the n sub-image regions, and $G_{ideal_1}$ to $G_{ideal_n}$ is represented as a curve or a function representing the reference pixel information corresponding to the n sub-image regions.

18. The method of claim 17, wherein at least one second period is performed until the compensation parameter update instruction is stopped, and whether the compensation parameter update instruction is stopped is determined by the at least one processor based on a duration set by the user.

19. The method of claim 8, wherein the preset threshold is in a range of 2%-10%.

20. The method of claim 9, wherein the weighted sum of the compensation parameters of the previous ultrasound image and the current compensation parameters is determined according to a formula below:

$$S_i = aC_{curr_i} + bC_{pre_i},$$

where $S_i$ refers to a weighted sum corresponding to the i-th sub-image region of the previous ultrasound image, $C_{curr_i}$ refers to the current compensation parameter corresponding to the i-th sub-image region of the previous ultrasound image, $C_{pre_i}$ refers to a compensation parameter of the previous ultrasound image corresponding to the i-th sub-image region, and a and b refer to weights of the compensation parameters of the previous ultrasound image and the current compensation parameters corresponding to all sub-image regions, respectively, wherein when there are n sub-image regions in the previous ultrasound image, $S_1$ to $S_n$ refers to a curve or a function representing the weighted sum corresponding to the n sub-image regions, $C_{curr_1}$ to $C_{curr_n}$ refers to a curve or a function representing the current compensation parameters corresponding to the n sub-image regions, $C_{pre_1}$ to $C_{pre_n}$ refers to a curve or a function representing the compensation parameters of the previous ultrasound image corresponding to the n sub-image regions, and a and b refers to weights of the $C_{curr_i}$ and the $C_{pre_i}$, respectively.

* * * * *